United States Patent [19]

Belcher et al.

[11] 4,066,897
[45] Jan. 3, 1978

[54] CHEMICAL CHANGE MEASURING APPARATUS

[76] Inventors: Ralph L. Belcher, 10603 Lorain Ave., Silver Spring, Md. 20901; Harry R. Wood, 13331 Query Mill Road, Gaithersburg, Md. 20760

[21] Appl. No.: 661,107

[22] Filed: Feb. 25, 1976

[51] Int. Cl.$^2$ ............................................. G01N 23/06
[52] U.S. Cl. .................................. 250/358 R; 250/360
[58] Field of Search ............... 250/252, 308, 358, 359, 250/360

[56] References Cited

U.S. PATENT DOCUMENTS

| | | | |
|---|---|---|---|
| 2,097,760 | 11/1937 | Failla | 250/359 |
| 2,304,910 | 12/1942 | Hare | 250/308 |
| 2,885,557 | 5/1959 | Kizaur | 250/360 |
| 3,148,279 | 9/1964 | Skala | 250/359 |
| 3,569,708 | 3/1971 | Weinbaum et al. | 250/360 |
| 3,769,507 | 10/1973 | Kenney et al. | 250/360 X |
| 3,840,746 | 10/1974 | Kehler | 250/360 |

Primary Examiner—Archie R. Borchelt
Attorney, Agent, or Firm—Witherspoon, Lane & Hargest

[57] ABSTRACT

This invention relates to testing to determine the residual recoverable energy of a battery of cells or a single cell, without requiring any electrical connection to the battery or the addition of special materials, substances, or devices to the intrinsic cell, and therefore, the remaining useful life of the battery or single cell. Two different embodiments, both of which rely on the fact that the electrodes of a battery or cell undergo chemical change during discharge, are disclosed. In the first embodiment, gamma radiation is transmitted through an electrode of the battery or cell and the level of the radiation exiting from the electrode is measured. This measurement is correlated with a known value obtained for that battery or cell before discharge has taken place. The second embodiment utilizes a beta or photon backscattering technique. A battery or cell undergoing test is subjected to beta or photon radiation and the backscatter is measured. This backscatter measurement is correlated with the value obtained from the backscatter measurements taken before any discharge of that battery or cell has taken place.

25 Claims, 3 Drawing Figures

FIG. I.

CHEMICAL CHANGE MEASURING APPARATUS

BACKGROUND OF THE INVENTION

This invention relates to battery or cell testing; and more particularly, to the measuring of the remaining capacity, and therefore the useful remaining life, of a battery of cells or a single cell.

Various battery or single cell testing devices are, of course, available on the market and have been available for some time. However, to applicant's knowledge, no easily operated testing device that provides a measure of the remaining capacity, and therefore the remaining useful life, of a battery cell has been devised.

Knowledge of the remaining capacity of a battery or cell provides more significant information about that battery or cell than can be provided by a tester that merely indicates, for example, whether the battery or cell is good, bad or weak. If a battery or cell checks "good" with such a tester, all that one knows about that battery or cell is that it was good at the time the test was made. The tested battery or cell may have very little remaining capacity and would under load become completely discharged or discharged to a useless level in a very short period of time after the good-bad test was performed. Thus, even though this battery or cell tested out as good, it really was nearly exhausted. Normally, one would not want to purchase such a battery or cell and normally would not purchase such a battery or cell if he was aware of the fact that very little capacity remained. Further, one would normally not want to use such a battery or cell in a piece of battery operated equipment knowing that the battery or cell would have to be replaced very shortly. Insofar as is known by applicants, no remaining capacity battery or cell testing devices that can be operated by lay persons have been devised prior to this invention.

Various systems and methods have been devised for measuring the remaining capacity of a battery or cell. These prior art systems generally require trained personnel to perform the remaining capacity test and generally laboratory type systems that are not very adaptable to general commercial or industrial use.

This invention provides battery or cell testing apparatus that can be operated by lay persons. The apparatus of this invention is relatively simple and therefore, a battery or cell tester designed according to this invention is suitable for general commercial and industrial uses. Further, by providing appropriate known metering devices, a direct read out of the remaining capacity can be obtained. In addition to being specifically utilized as a battery or cell testing device, the two embodiments of this invention can be used to measure the chemical change that has taken place in any device that undergoes a chemical change wherein the reaction products are spatially separated; and therefore, the invention has broader utility than just a battery or cell tester.

SUMMARY OF THE INVENTION

A first embodiment of the invention utilizes gamma radiation to measure the remaining capacity of a battery or a single cell. A gamma radiation producing isotope is enclosed in a housing having an aperture. A battery or cell is so positioned relative to the aperture that the beam of gamma rays leaving the housing through this aperture passes through an electrode of the battery or cell. A gamma ray detector is positioned on the opposite end of this electrode to detect the gamma rays that exit from the electrode after passing through the electrode. The output of the gamma ray detector is coupled to processing and measuring equipment to provide a measurement of the remaining capacity of the battery or cell under test.

The second embodiment of the invention utilizes beta or photon backscattering techniques. A source of beta or photon radiation is directed onto an electrode of a battery or cell and the backscatter from the electrode is detected, processed and measured to provide a measurement of the remaining capacity of the battery or cell.

Both embodiments of the invention relay on the fact that electrodes of a battery or cell undergo chemical change during discharge of the battery or cell. The attenuation of the gamma rays, beta rays or photons varies with the chemical nature of the material subjected to the radiation. Therefore, as the chemical nature of the electrodes of a battery or cell changes during discharge, the level of radiation detected by either of the two embodiments varies with the degree of chemical change which is directly related to the state of discharge of the battery or cell. The measurement obtained for any given battery or cell is correlated with a known value for that battery or cell before any discharge has taken place. This correlation can be accomplished directly by appropriate metering equipment is that a direct read out of the state of discharge is obtained.

There are, of course, devices other than batteries or single cells that undergo chemical changes. The two embodiments of this invention can also be utilized to measure the chemical state of these other devices. Therefore, while the invention is specificaly described herein with reference to the testing of a battery of cells or the testing of a single cell, it is to be remembered that the invention has broader utility.

BRIEF DESCRIPTION OF THE DRAWING

A complete understanding of the structural details and operation of the invention can be obtained from the following detailed description of the invention when read in conjunction with the annexed drawing in which.

DETAILED DESCRIPTION OF THE INVENTION

Figure 1:
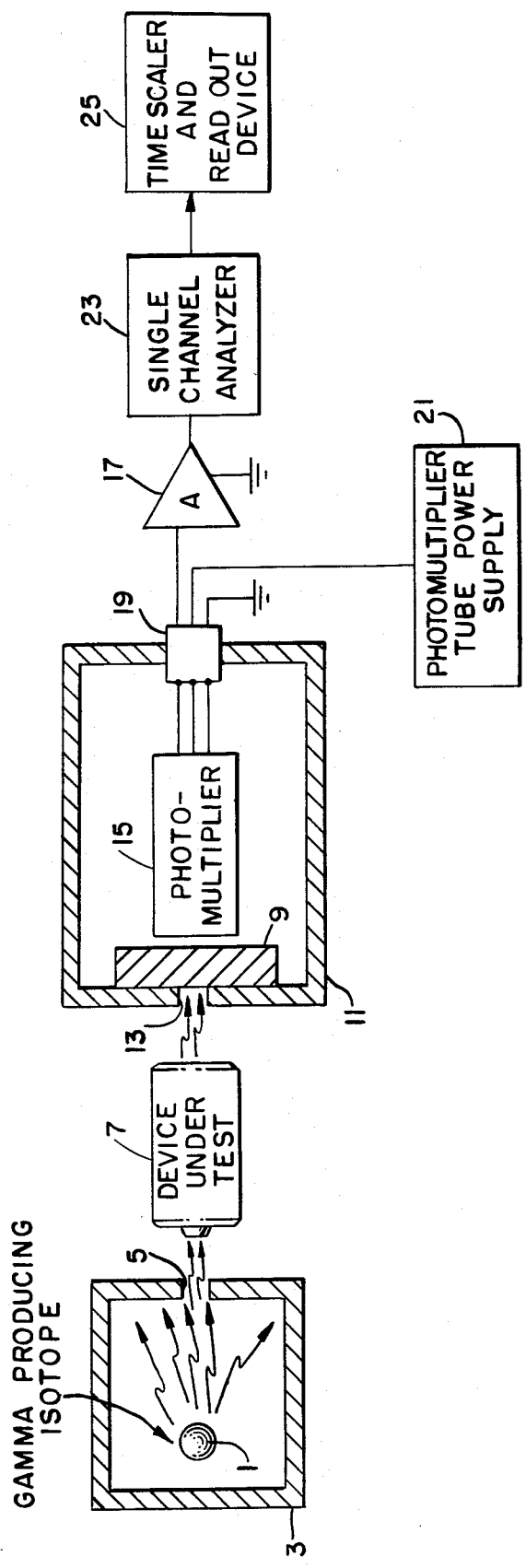
FIG. 1 is a block diagram showing the gamma radiation embodiment of the invention.

FIG. 1 shows the gamma radiation embodiment of the invention. A gamma radiation producing isotope 1 is housed in an enclosure 3 (shown in cross-section). Enclosure 3 is made of a high density shielding material such a lead [Pb] and an aperture 5 in one of its walls. The gamma ray beam produced by isotope 1 radiates out of enclosure 3 through aperture 5. Aperture 5 is sized in both diameter and length to optimize the collimating function. Other known collimating structures or schemes for this radiation are obvious extensions of this approach.

The battery, cell or device to be tested is so positioned that an element of the battery, cell or device, an element that undergoes a chemical change, is aligned with aperture 5. In FIG. 1, a single cell 7, such as a conventional D-cell, is shown with the center electrode, the anode, of cell 7 aligned with aperture 5. In FIG. 1, aperture 5 is shown as merely being a hole in one of the walls of enclosure 3. In practice, aperture 5 will actually be an adjustable aperture, in that the opening can be varied to accommodate various battery sizes and geometric configurations. Such adjustable apertures are well known in the art. Thus, the size of aperture 5 would be adjusted such that the collimated beam exiting from aperture 5 passes through the center electrode of cell 7 when cell 7 is placed in the apparatus for testing.

A gamma radiation detector 9 which may be a sodium iodide (NaI) crystal is secured inside the enclosure 11 (shown in cross-section). Enclosure 11 is also made from a high density shielding material such as lead [Pb]. Detector 9 is secured inside enclosure 11 such that it covers the aperture 13 cut in one wall of the enclosure 11. Detector 9 produces photons of light in response to gamma rays striking detector 9. A photomultiplier 15 is placed behind detector 9 to detect the light emanating from detector 9. It is a straight forward extension of this technique to utilize known radiation detection systems in place of sodium iodine (detector 9) and photomultiplier 15 for this purpose.

The output of photomultiplier 15 is coupled to a linear amplifier 17 through a conventional coupling device 19. Electrical power for photomultiplier 15 is provided by the power supply 21 through coupler 19. The output of amplifier 17 is coupled to the input of a single channel analyzer 23 and the output of single channel analyzer 23 is coupled to the input of a time scaler and read out device 25.

When cell 7 is placed in the apparatus as shown in FIG. 1, the collimated beam of gamma rays passing through aperture 5 pass through the center electrode. These rays are attenuated by this electrode. Thus, the radiation flux leaving the center electrode is at some value less than the flux of the gamma rays entering this electrode. The gamma radiation leaving the center electrode of cell 7 is detected by detector 9. Detector 9 is conveniently a sodium iodide crystal but can be any suitable detector. The light intensity emitted by detector 9 is directly related to the energy level of the rays striking detector 9. Photomultiplier 15 converts the light energy to an electrical signal which is directly related to the level of the light emanating from detector 9. Amplifier 17 merely amplifies the signals from photomultiplier 15 to a suitable level for processing by single channel analyzer 23. Single channel analyzer 23 discriminates against all signals outside of a preset range. This preset range is directly proportional to the energy of the selected gamma rays emitted by the isotope source selected.

The time scaler and read out device 25 receives the signals from single channel analyzer 23 and processes these signals to obtain a read out of the remaining capacity of cell 7. More specifically, the time scaler circuitry of the time scaler and read out device 25 sets a time window during which the signals from single channel analyzer 23 are observed. A fixed amount of time (time window) is necessary since the number of detectable photons per unit of time produces an uncertainty which is best resolved by integration over several time periods. The output of the time-scaler part of the time-scaler and read-out device 25, is then applied to the read-out part of device 25 which provides a read out of the remaining capacity of cell 7.

As a battery or cell is discharged, the electrodes of that battery or cell undergo chemical change. The level of gamma radiation exiting from the center electrode of cell 7 is directly related to this chemical change. Thus, the level of gamma radiation exiting from the center electrode of cell 7 varies with the state of discharge of the cell under test.

When a battery or cell is fully charged, the gamma radiation passing through the electrode placed in the path of the radiation, the electrode of cell 7 in FIG. 1, is determined by the relationship $I = Io \exp[-MX]$ where $M$ is the linear absorption coefficient of the electrode, $Io$ is the strength of the gamma source, and $X$ is the length of the electrode structure (the anode of cell 7 in this case) through which the radiation passes. Thus, the strength of the radiation falling upon detector 9 as a percentge of the incident radiation from isotope source 1 can be expressed as $I/Io$. As cell 7 discharges, its electrodes undergo chemical changes which cause a change in the attenuation of the gamma radiation. The attenuating mechanism being a combination of absorption and scattering out of the detection range, both on an energy and spatial basis, is dependent on the atomic number (Z) of the electrode under test. As the battery or cell is discharged, the attenuation rises, due to the chemical change that takes place in the electrode in the radiation path, thereby yielding a percentage [I/Io] change as compared to the attenuation when the battery or cell is fully charged. Thus, detector 9 detects the level of radiation exiting from the anode of cell 7 in FIG. 1 and the output of detector 9 is processed by photomultiplier 15, amplifier 17, single channel analyzer 23 and time scaler and read out device 25 to provide a percentage change reading which can be translated on a scale provided with the read out part of device 25 as a reading of the remaining capacity of cell 7. This scale represents the remaning capacity of cel 7 as a percentage or as a fraction of full capacity, for example.

Figure 3:
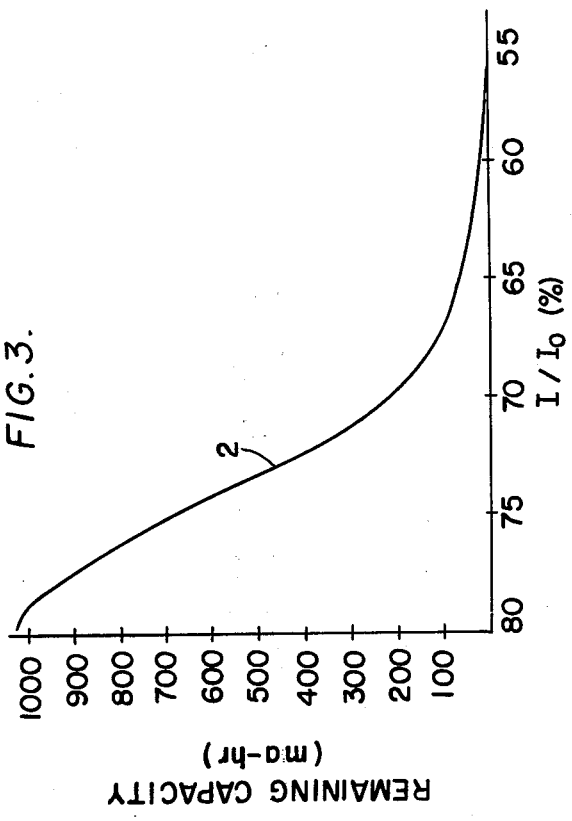
FIG. 3 is a graph of the remaining capacity of a specific mercury-zinc cell versus percentage absorption of gamma radiation through an electrode of the cell.

The fact that the remaining capacity of a battery or cell can be measured by measuring the percentage of attenuation change of the gamma radiation as compared to the attenuation at full charge by the apparatus of FIG. 1 is illustrated in FIG. 3 which shows a remaining capacity versus the percentage change [I/Io (%)] curve for a specific cell. The curve in FIG. 3 is for a Mallory Rm-134 mercury-zinc cell. This cell was placed in the apparatus such that its center electrode (the zinc anode) was aligned in the radiation path of the gamma rays. In other words, cell 7, as oriented in FIG. 1, can be considered as this mercury-zinc cell. A reading for the mercury-zinc cell was first obtained at full charge and this reading was plotted in the graph of FIG. 3. The mercury-zinc cell was then discharged and test measurements were made with the apparatus of FIG. 1 at several levels of discharge down to complete discharge and the measurement for each test was plotted. The various test measurements points plotted in the graph were then joined to form the curve 2 which clearly illustrates that the percentage of attenuation I/Io increases as the cell was discharged. At full charge, approximately 79% of the gamma radiation from gamma producing isotope 1 traveled through the zinc anode and impinged on detector 9; or stated conversely, for a fully charged Mallory RM-134 mercury-zinc cell, the level of radiation exiting from the zinc anode is 21% less than the level of radiation entering the zinc anode from aperture 5. When this cell had only approximately one-half of its capacity remaining, a little more than 73% of the radiation from gamma radiation producing isotope 1 reached detector 9. That is, as the zinc of the anode changed to zinc oxide during discharge, the attenuation of the gamma radiation by the anode increased from approximately 21% at full charge to approximately 27% at ½ of full capacity. At one-tenth of the remaining capacity, the attenuation increased from the approximately 21% at full capacity or charge to approximately 33% and at complete discharge from the approximately 21% at full charge to approximately 45%.

From the curve 2 of FIG. 3 and the above discussion of the curve, it should be obvious that the read out part of time scaler and read out device 25 merely needs to be a meter that translates the level of radiation incident on detector 9 as compared to the level at full charge in terms of remaining capacity. Of course, the meter has to be calibrated in terms of full capacity for each different battery or cell since the level of radiation incident on detector 9 is dependent on the electrode material and the length of the electrode structure of each battery or cell of a given level of radiation emanating from aperture 5. This can be readily accomplished by providing the meter with a switch or switches that are set on the appropriate contacts for the particular battery or cell under test. There are various types of known meters that will provide this desired read out. In this respect, it should be pointed out that all the elements of the apparatus of FIG. 1 are well known elements available on the market. Further, there are various different types of detectors, photomultipliers, amplifiers, etc. available on the market that can be used. The specific elements chosen need merely be capable of performing the desired function in the apparatus. However, the choice of the gamma producing isotope is limited to those isotopes that produce low energy gamma radiation, thereby optimizing the previously defined MX product.

The operation of the apparatus of FIG. 1 as described above depends upon the use of low energy level gamma radiation. With high energy gamma radiation, greater shielding of the isotope would be required and greater shielding of enclosure 11 to shield detector 9 from stray gamma radiation would be required. Further, with high energy radiation producing isotopes, the difference between measurements obtained for fully charged battteries or cells and the measurements obtained with these same batteries or cells discharged either partially or fully would in most cases not be discernible. The level of output of detector 9 would be high at all times. Thus, the gamma radiation producing isotope use for isotope 1 should be one that produces low energy gamma radiation, such as Iridium-192 (0.430 Mev) or Americium-241 (0.057 Mev), for example. There are, of course, other low energy gamma radiation producing isotopes that can be used. High flux gamma radiation producing isotopes could also be used with attenuators between the isotopes and aperture 5. However, the use of such high flux producing isotopes would also greatly increase the shielding requirements and thus make the use of high flux gamma radiation producing isotopes impractical, particularly since suitable iotopes are readily available.

While the apparatus of FIG. 1 has been described as being used for measuring the chemical change and thereby determining the remaining useful life of a single cell, or a battery, the apparatus can also be used for measuring the chemical change that has taken place in any device that undergoes a chemical change wherein the reaction products are spatially separated. Cell 7 is merely replaced by the device that is to be tested. The apparatus operates in the same manner as described above with reference to cell 7 for any device that is to be tested. The measurement obtained for the particular device is merely correlated with a known value obtained when the type of device being tesed was fresh (i.e., before the device undergoes any substantial chemical change). Thus, in the broader sense, cell 7 is to be considered as any device that undergoes a chemical change.

Figure 2:
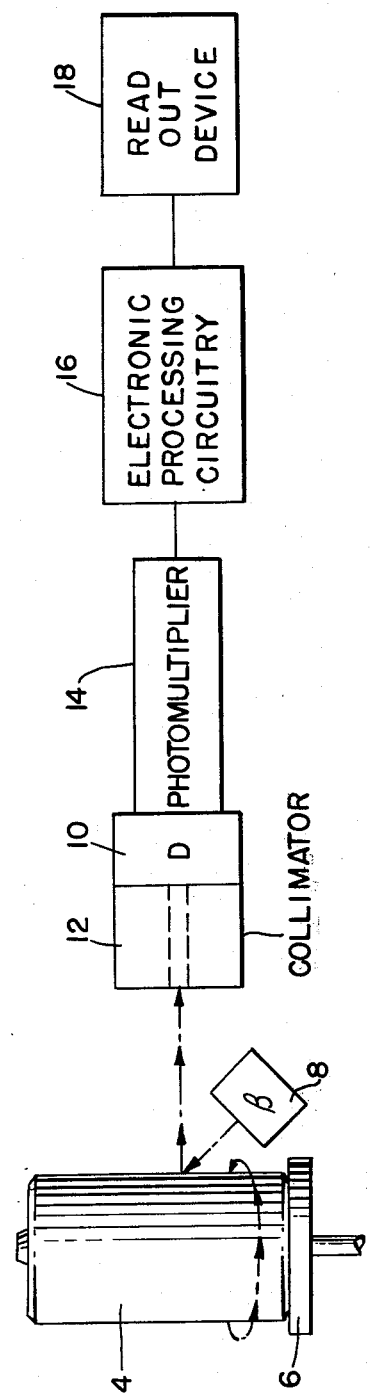
FIG. 2 is a block diagram showing the beta or photon backscattering embodiment of the invention.

FIG. 2 shows a second embodiment of the invention. This embodiment relies on backscattering of beta rays or photons to measure the remaining capacity of a battery or a single cell. This embodiment is limited in use to those batteries or cells in which the outer casing serves as an electrode or an electrode support. The battery or cell 4 in which the casing is an electrode under test is placed on a turntable 6 and slowly rotated Beta or photon radiation from any suitable source 8 is directed onto the battery. The backscatter from the outer electrode of battery or cell 4 is directed onto a detector 10, which may be a sodium iodine detector for gamma radiation or a ionization chamber for Beta radiation or any other suitable radiation detector, by means of the collimator 12.

In response to the radiation, sodium iodine detector 10 emits photons of light and this light is detected by the photomultiplier 14. The output of photomultiplier 14 is coupled to the electronic processing circuitry 16 which is preferably identical to the processing circuitry of FIG. 1 (amplifier 17, single channel analyzer 23 and the time scaler part of time scaler and read out device 25). The output of electronic processing circuitry 16 is coupled to a suitable read out device 18 which can be identical to the read out device used in FIG. 1.

The embodiment of FIG. 2 also relies upon the fact that the electrodes of a battery or cell undergo chemical change as the battery or cell discharges and relies upon the fact that the intensity of the backscatter radiation varies with this chemical change. Thus, to obtain a read out of the remaining capacity of a battery or cell under test, the apparatus of FIG. 2 measures the backscatter from the battery or cell under test and correlates or, in effect, compares this measurement with the measurement obtained when this particular type of battery or cell is fully charged.

As was previously mentioned, the embodiment of FIG. 2 is limited to those batteries or cells where the outer casing serves as one of the electrodes or electrode support. From the foregoing description of this embodiment, the reason for this should be obvious. However, the reason for rotating the battery or cell under test may not be obvious. If the physical characteistics of a given material are uniform throughout the entire material and if the distance between a source and detector of backscattering apparatus and a surface of this material remains constant, then the backscatter measurement at any point along that surface of the given material should be constant. In a given cell or battery, the electrode material may be absolutely uniform over its entirety and as the battery or cell is discharged the degree of chemical change over the entire electrode may not be uniform. Further, with the battery or cell case serving as an electrode and as the subject electrode for conducting the backscatter measurements, there is always a danger that the casing may have slight indentations caused by improper handling and shipping. If the case does have a slight indentation, the distance between the surface at this indent and the backscattering apparatus is different than at the distance where no indent is present. A change in the distance between the surface of a material and the backscattering apparatus changes the level of the detected backscatter. By rotating the battery, measurements of the backscatter are obtained over a given area of the electrode rather than at just one point. These measurements are then averaged by conventional averaging circuitry in read out device 18 to obtain a measurement for the battery or cell under test. Thus, any variations in the physical characteristics of the electrode when the battery is fully charged should average out and similarly, any variations in the physical characteristics and any variations in the chemical change over the electrode due to partial or full discharge should be averaged out thereby providing reproducible accurate measurements. If the battery or cell casing has a readily visible, rather large indent, one should avoid taking any measurements in the area of the indent.

While rotation of the battery or cell is desirable with the embodiment of FIG. 2 in order to obtain reproducible accurate measurements, measurements having a reasonable degree of accuracy could be obtained without rotating the battery or cell by insuring that any measurement is always taken at the same point on the electrode. This can be accomplished by providing a visible test point mark and aligning the mark with the measuring apparatus. However, a higher degree of accuracy is obtained by rotating the battery or cell and therefore such rotation is desirable. Further, if the electrode is indented in the area of such a test mark, no accurate measurement can be obtained.

While the apparatus of FIG. 2 is limited to those batteries or cells where the outer casing serves as an electrode or electrode support, the apparatus of FIG. 2 is not limited to use with batteries or cells alone. Any device in which the outer surface is an element that undergoes a chemical change or in which the outer surface supports such an element can be tested by the apparatus of FIG. 2. Such a device is merely substituted for cell 4 and the operation is the same as described above with reference to cell 4.

While the two embodiments of the invention have been described with reference to measuring the remaining capacity of a battery or a single cell, it should be obvious that these two embodiments could also be used for quality control purposes in the manufacturing of batteries or single cells. The test is made without any discharge of the battery or cell tested, without requiring any addition of special substance, materials, or devices to the basic cell or battery or for quality control purposes in the manufacture of other devices that undergo a chemical change wherein the reaction products are spatially separated.

While the invention has been shown and described with reference to two specific embodiments, it will be apparent to those skilled in the art that various changes and modifications can be made to the embodiments shown and described without departing from the spirit and scope of the invention as defined in the claims.

It is claimed that:

1. A method for measuring the degree of chemical change that has taken place in a device that undergoes chemical change wherein the reaction products are spatially separated comprising the steps of:
    a. utilizing a beam of low energy gamma rays of a known energy level;
    b. placing the device whose chemical change is to be measured in the path of said beam of gamma rays such that an element of said device is aligned with said path of said beam of gamma rays such that said gamma rays travel through said element;
    c. detecting the level of said gamma rays exiting from said element;
    d. generating electrical signals in response to the detected level of said gamma rays exiting from said element;
    e. electronically processing said generated electrical signals to produce measuring signals indicative of the degree of chemical change that has taken place in said device;
    f. producing a read out; and
    g. correlating said read out with a known value obtained before said device that undergoes a chemical change has undergone any chemical change to thereby obtain a measure of the change that has taken place in said device that undergoes a chemical change.

2. A method of measuring the degree of chemical change that has taken place in a device that undergoes chemical change wherein the reaction products are spatially separated comrpising the steps of:
    a. placing said device on a turntable;
    b. rotating said turntable;
    c. impinging radiation of a known energy level on a surface of said device while said turntable is rotating;
    d. detecting the backscatter of said radiation from said surface of said device;
    e. generating electrical signals in response to said detected backscatter of said radiation;
    f. electronically processing said generated electrical signals to produce measuring signals indicative of the degree of chemical change that has taken place in said device;
    g. providing a read out in response to said measuring signals; and
    h. correlating said read out with a known value obtained before said device that undergoes a chemical change has undergone any chemical change to thereby obtain a measure of the change that has taken place in said device that undergoes a chemical change.

3. The method as defined in claim 1 wherein said device is a battery.

4. The method as defined in claim 2 wherein said devices is a battery.

5. A method for measuring the remaining capacity of a battery comprising the steps of:
    a. transmitting gamma radiation of a known energy level through an electrode of said battery;
    b. measuring the attenuation of said gamma radiation by said electrode; and
    c. correlating said measured attenuation with a standard value obtained for the type of said battery under test before any discharge has taken place to obtain a measurement of said remaining capacity of said battery.

6. A method for measuring the remaining capacity of a battery comprising the steps of:
    a. rotating said battery;
    b. directing beta radiation on a surface electrode of said battery while said battery is rotating;
    c. measuring the backscatter of said beta radiation from said surface electrode; and d. correlating said measured backscatter with a standard value obtained for the type of said battery under test before any discharge has taken place to obtain a measure of the remaining capacity of said battery.

7. Apparatus for measuring the degree of chemical change in a device that undergoes a chemical change wherein the reaction products are spatially separated comprising:
   a source of gamma radiation enclosed in a shielded housing having an aperture through which a collimated beam of low energy gamma rays is transmitted from said housing;
   a second shielded housing spaced apart from said first shielded housing and having an aperture therein, said aperture in said second shielded housing being aligned with said aperture in said first shielded housing;
   a device whose degree of chemical change is to be measured, said device being located between said first shielded housing and said second shielded housing such that an element of said device is aligned with said aperture in said first housing and said aperture in said second housing;
   a gamma radiation detector secured inside said second housing over said aperture in said second housing;
   a photomultiplier secured in said second housing and operatively associated with said gamma radiation detector; and
   electronic processing circuitry coupled to said photomultiplier.

8. The apparatus as defined in claim 7 wherein said electronic processing circuitry comprises: an amplifier coupled to said photomultiplier; a single channel analyzer coupled to said amplifier and a time scaler and read out device coupled to said single channel analyzer.

9. The apparatus as defined in claim 8 wherein said source of gamma radiation is a gamma radiation producing isotope.

10. The apparatus as defined in claim 9 wherein said detector is a sodium iodide crystal.

11. The apparatus as defined in claim 10 wherein said isotope is Iridium-192.

12. The apparatus as defined in claim 10 wherein said isotope is Americium-241.

13. The apparatus as defined in claim 7 wherein said device whose degree of chemical change is to be measured is a battery.

14. Apparatus for measuring the degree of chemical change that has taken place in a device that undergoes a chemical change wherein the reaction products are spatially separated comprising:
   a rotating turntable;
   a device whose degree of chemical change is to be measured, said device being placed on said rotating turntable;
   a source of radiation directed onto said container;
   a backscatter detection system positioned relative to said device and said source of radiation to detect the backscatter of said radiation from said container; and
   an electronic processing system coupled to said detection system.

15. The apparatus as defined in claim 14 wherein said detection system comprises: a collimator and a radiation detector.

16. The apparatus as defined in claim 15 wherein said electronic processing system comprises: a photomultiplier operatively associated with said radiation detector; an amplifier coupled to said photomultiplier; a single channel analyzer coupled to said amplifier; and a time scaler and read out device coupled to said single channel analyzer.

17. The apparatus as defined in claim 13 wherein said radiation detector is a sodium iodide crystal.

18. The apparatus as defined in claim 17 wherein said device whose degree of chemical change is to be measured is a battery.

19. Apparatus for measuring the remaining capacity of a battery comprising:
   a source of gamma radiation enclosed in a shielded housing having an aperture through which a collimated beam of low energy gamma rays is transmitted from said housing;
   a second shielded housing spaced apart from said first shielded housing and having an aperture therein, said aperture in said second shielded housing being aligned with said aperture in said first shielded housing;
   a battery whose remaining capacity is to be measured, said battery being located between said first shielded housing and said second shielded housing such that an electrode of said battery is aligned with said aperture in said first housing and said aperture in said second housing;
   a gamma radiation detector secured inside said second housing over said aperture in said second housing;
   a photomultiplier secured in said second housing and operatively associated with said gamma radiation detector; and
   electronic processing circuitry coupled to said photomultiplier.

20. The apparatus as defined in claim 19 wherein said electronic processing circuitry comprises: an amplifier coupled to said photomultiplier; a single channel analyzer coupled to said amplifier and a time scaler and read out device coupled to said single channel analyzer.

21. The apparatus as defined in claim 20 wherein said source of low energy gamma radiation is a gamma radiation producing isotope.

22. Apparatus for measuring the remaining capacity of a battery comprising:
   a rotating turntable;
   a battery whose container is one of its electrodes, said battery being placed on said rotating turntable;
   a source of radiation directed onto said container;
   a backscatter detection system positioned relative to said battery and said source of radiation to detect the backscatter of said radiation from said container; and
   an electronic processing system coupled to said detection system.

23. The apparatus as defined in claim 22 wherein said detection system comprises: a collimator and a radiation detector.

24. The apparatus as defined in claim 23 wherein said electronic processing system comprises: a photomultiplier operatively associated with said radiation detector; an amplifier coupled to said photomultiplier; a single channel analyzer coupled to said amplifier; and a time scaler and read out device coupled to said single channel analyzer.

25. The apparatus as defined in claim 24 wherein said source of radiation is a beta radiation source.

* * * * *